United States Patent
Schierstedt

(10) Patent No.: US 8,691,294 B2
(45) Date of Patent: Apr. 8, 2014

(54) CISTUS EXTRACTS

(75) Inventor: Detlef Schierstedt, St. Augustin (DE)

(73) Assignee: Krewel Meuselbach GmbH (DE)

( * ) Notice: Subject to any disclaimer, the term of this patent is extended or adjusted under 35 U.S.C. 154(b) by 119 days.

(21) Appl. No.: 13/449,816

(22) Filed: Apr. 18, 2012

(65) Prior Publication Data

US 2012/0201866 A1 Aug. 9, 2012

Related U.S. Application Data

(62) Division of application No. 12/525,312, filed on Aug. 3, 2009, now abandoned.

(30) Foreign Application Priority Data

Feb. 2, 2007 (DE) .......................... 10 2007 006 122
Jan. 28, 2008 (WO) ................. PCT/EP2008/050966

(51) Int. Cl.
*A01N 65/00* (2009.01)

(52) U.S. Cl.
USPC ........................................................ 424/725

(58) Field of Classification Search
None
See application file for complete search history.

(56) References Cited

U.S. PATENT DOCUMENTS 6,664,289 B2 12/2003 Hansen

FOREIGN PATENT DOCUMENTS

| DE | 202005014459 U1 | 2/2006 |
| EP | 1837029 A1 | 9/2007 |
| WO | 2007/031297 A2 | 3/2007 |
| WO | 2008/092826 A3 | 8/2008 |

OTHER PUBLICATIONS

K. Bauer, K-H Fromming, C. Fuhrer "Pharmazeutische Technologie" 1991, Georg Thieme Verlag, Stuttgart, XP-002505509 Seite 251, Abbildung 11.5.
Viren fordern das Imunsystem, Urheimische Notizen, 4 Augaben jahrlich ISSN 1612-0728.
Cystus 052 Gurgellosung.
Cystus 052 Infekblocker Tabletten.
Deutsche Apothekerzeitung, Nr. 146.
Zakay-Rones; A. et al., "Inhibition of Several Strains of Influenza Virus in vitro and Reduction of Systems by an Elderberry Extract", The Journal of Alternative and Complementary Medicine, 1995, 1 (4) 361-369.
Pieroni, A., et al., "Natural Remedies and Nutraceuticals used in Ethnoveterinary Practices in Inland Southern Italy", Veterinary Research Communications, 2004, 28 (1), 55-80.
Petereit, F. et al, "Flavan-3-ols and Proanthocyanidins From *Cistus incanus*", Phystochmistry 1991, 30 (3), 981-985.
Attaguile, G., et al., Antioxidant activity and protective effect on DNA cleavage of extracts from *Cistus incanus* L. and *Cistus monspeliensis* L., CellBiol. Toxicol 2000, 16 (2) 83-90.
Bouamama, N., et al., "Antibacterial and antifungal activities of *Cistus incanus* and *C. monspeliensis* leaf extracts", Therapie 1999, 54 (6) 731-3.

*Primary Examiner* — Michael Meller
(74) *Attorney, Agent, or Firm* — Clements Bernard PLLC; Gregory N. Clements

(57) ABSTRACT

The present invention relates to the use of a nasal spray made from *Cistus* extracts for the prevention and/or treatment of viral and/or bacterial diseases of the oral and pharyngeal cavities.

1 Claim, No Drawings

CISTUS EXTRACTS

The present invention relates to the use of a nasal spray made from *Cistus* extracts for the prevention and/or treatment of viral and/or bacterial diseases of the oral and pharyngeal cavities.

Influenza, also known under the designation "flu", is a contagious viral disease that spreads around the world in seasonal epidemics. Three virus types A, B and C are distinguished. B and C are restricted to humans, while type A extends over mammals and birds.

DE 20 2005 014 459 U1 relates to an aerosol containing an extract from plants of the genus *Cistus*.

EP 1 837 029 A1 describes a nasal spray that essentially contains an extract from *Cistus* plants.

Since the therapeutic target of aerosols is essentially the lung, an intolerance may occur in sensitive subjects, for example, allergic persons. The question of how the extract components entering the lung are eliminated from the body, especially upon prolonged application, is also still unsettled.

Usually, different deposition mechanisms are distinguished. Therefore, the particle size for sprays designed for the nasal, oral or pharyngeal cavity should be >30 µm in order to prevent that drugs enter the lung. The situation is different if the drugs are to reach the smallest bronchioles of the lung by inhalation. In this case, the optimum particle size range is from 0.5 to 5 µm.

Antiviral medicaments are effective in the prophylaxis of a viral disease and in the treatment thereof. The direct medicinal cure of a viral disease has not yet been successful.

Further, an elderberry extract is known for its activity of shortening the duration of an influenza under certain circumstances, but without exhibiting a significant preventive effect (Zakay-Rones, Z.; Varsano, N.; Zlotnik, M.; Manor, O.; Regev, L.; Schlesinger, M.; Mumcuoglu, M. J. Altern. Complement. Med. 1995, 1 (4), 361-9).

A germicidal and antiviral activity is also known for extracts from plants, of the genus *Cistus*. The *Cistus* species *incanus* and its subspecies *tauricus*, both of which are widespread in the Mediterranean region, have been used already in the traditional medicine of this region. In animal keeping, *Cistus incanus* has been used as a natural cure and generally for increasing the health status of animals (Pieroni, A.; Howard, P.; Volpato, G.; Santoro, R. F. Vet. Res. Commun. 2004, 28 (1), 55-80). In Northern parts of Greece, *Cistus incanus* ssp. *tauricus* was traditionally used for the treatment of skin diseases (Petereit F., Kolodziej H.; Nahrstedt A. Phytochemistry 1991, 30 (3), 981-985).

*Cistus* species contain among others flavanoids and proanthocyanidines (Petereit F., Kolodziej H., Nahrstedt A. Phytochemistry 1991, 30 (3), 981-985), which may act as antioxidants in the body (Attaguile, G.; Russo, A.; Campisi, A.; Savoca, F.; Acquaviva, R.; Ragusa, N.; Vanella, A. Cell Biol. Toxicol. 2000, 16 (2), 83-90). Extracts from the leaves of *Cistus incanus* have an antibacterial and antimycotic activity (Bouamama, N. et al. Theraple 1999, 54 (6), 731-3).

Therefore, it is the object of the present invention to provide an agent for the prevention and/or treatment of viral diseases, for example influenza and common cold, that can be prepared inexpensively and does not cause any side effects upon administration.

This object is achieved by the use of extracts from plants or plant components of the genus *Cistus* for the preparation of a nasal spray for the prevention and/or treatment of viral and/or bacterial diseases of the nasal and/or pharyngeal cavities.

In a first embodiment, the invention thus relates to nasal sprays made from extracts from plants or plant components of the genus *Cistus* having a particle size of at least 30 µm for the prevention and/or treatment of viral and/or bacterial diseases of the nasal and/or pharyngeal cavities.

Surprisingly, it has been found that a *Cistus* nasal spray yields comparable prophylactic effects, but lacks the above described drawbacks.

Due to the particle size of the nasal sprays according to the invention, they are not respirable, but act in the oral, nasal and pharyngeal cavities whereas aerosols, having smaller particle sizes, do not display an action there, or only a small one. The particle size as desired according to the invention can be prepared by commercially available atomizers and pump sprays.

Sprays within the meaning of the present invention include those having a content of antibiotics, vasoconstrictors, for example, oxymetazoline or xylometazoline hydrochloride, which cause the nasal mucosa to decongest, for example, in colds, so that breathing through the nose more freely is possible again. However, in addition to the ethical nasal sprays, medicinal products acting on a purely physical base and contain physiological saline, for example, can also be prepared.

In a preferred embodiment, the nasal sprays according to the invention contain preservatives in order to extend the storage stability of the nasal sprays and thus to enable several administrations over an extended period of time, such as several weeks or months. This is preferred because repeated applications over an extended period of time are necessary especially for prevention.

As the preservative, for example, benzalkonium chloride, which is often employed in the field of nasal drops, may be used. Surprisingly, however, it has been shown that the preservatives benzoic acid and sorbic acid, which are employed less frequently, result in a significant extension of the storage stability as compared to benzalkonium chloride. In addition to the free acids as such, their partially or completely neutralized salts may also be added to the nasal sprays.

The extract is obtained from a plant of the genus *Cistus*. Of the genus *Cistus*, about 20 species are known:

*C. albidus* L.
*C. chinamadensis* Banares & P. Romero
*C. clusii* Dunal
*C. crispus* L.
*C. heterophyllus* Desf.
*C. incanus* (also referred to as *C. creticus*)
*C. inflatus* Pourr. ex Demoly (also referred to as *C. hirsutus* Lam. or *C. psilose-palus* Sweet)
*C. ladanifer* L.
*C. laurifolius* L.
*C. libanotis* L.
*C. monspeliensis* L.
*C. munbyi* Pomel
*C. ochreatus* Chr. Sm. ex Buch
*C. olsbeckiifolius* Webb ex Christ
*C. parviflorus* Lam.
*C. populifolius* L.
*C. pouzolzii* Delile
*C. salviifolius* L.
*C. sintenisfi* Litard. (also referred to as *C. albanicus* E. F. Warburg ex Heywood)
*C. symphytifolius* Lam.

Preferably, the extract is obtained from the species *C. incanus*. *C. incanus* includes two subspecies, *C. incanus* ssp. *tauricus* and *C. incanus* ssp. *undulates*. Of these, the subspecies *C. incanus* ssp. *tauricus* is used more preferably for extraction.

The extract is obtained, in particular, from the aerial parts of the plants. Preferably, the aerial shoots of the plants regrown in the same year are employed. The plant parts are subjected to extraction immediately after harvest, i.e., in a raw state. Alternatively, the plant parts are dried before the extraction. Subsequently, the leaves of the plant are suitably comminuted, for example, by attrition or cutting.

The extraction is effected with a suitable solvent. Suitable solvents include aqueous or organic solvents, especially water, alcohols, such as methanol, ethanol or isopropanol, or chlorinated solvents, such as dichloromethane, and acetone, acetylacetone, ammonia, carbon dioxide or glacial acetic acid. Mixtures of the mentioned solvents may also be employed. Preferably, a mixture of water with methanol or ethanol is employed.

The extraction is usually performed at room temperature. However, it is also possible to perform the extraction at elevated temperatures of from 25° C. to the boiling point of the solvent employed. Extraction at room temperature is preferred.

In order to achieve as high a yield as possible, the plant material can be extracted several times. Also, different solvents may be employed in the different extraction steps.

Aqueous extracts may be diluted or further processed without diluting. Organic or organic-aqueous extracts are usually freed from solvent and processed into dry extracts. The dry extracts are then processed into the nasal sprays according to the invention.

The above mentioned liquid or dry extracts can be employed for the prevention and/or treatment of influenza after adding per se known auxiliary agents and additives.

Before being processed into a medicament, the raw product may also be concentrated and/or further processed. The processing may include, for example, purification steps familiar to the skilled person, such as centrifugation, filtration and decanting, in order to remove suspended matters from the extract.

The extract described is preferably employed for the prevention and/or treatment of influenza, especially common cold, flu, flu-like infections, for example, bird flu.

The packaged medicaments or medicinal products within the scope of the present invention may contain the usual galenic auxiliaries, such as preservatives and/or solvents. The extract may be contained in a concentration of from 1 µg/ml to 100 mg/ml, preferably from 25 µg/ml to 50 mg/ml.

Since the mechanism of action seems to be physical and resistances are thus unlikely, rock rose (*Cistus*) preparations are excellently suitable for both the treatment and prophylaxis of viral infections in the upper respiratory tract. If known preparations, medicinal products or food supplements are employed in the form of sucking tablets or teas, viral prophylaxis in the pharyngeal cavity is achieved with these dosage forms, but viruses are not prevented from still entering through the nose and proliferating after sewing in the nasopharyngeal cavity.

However, with the present invention, it is possible to prevent the viruses from entering and settling in the nose.

Surprisingly, it has been found that a nasal spray with a rock rose extract can reduce the risk of infection with colds.

Seven subjects, who had at least one common cold in the period of 3 months, used the nasal spray according to the invention in the same period of the following year about ten times a day. In this period, only one became ill.

EXAMPLES

The preparation of the extracts from *Cistus tauricus* is effected by analogy with the Example of DE 20 2005 014 459 U1 with 50% by volume of ethanol at a drug-to-extract ratio of 4:1.

The preparation of a *Cistus* decoction is performed by pouring 1000 ml of hot water over 10 g of *Cistus* herb, followed by filtration after 5 min.

Example 1

100 ml of nasal spray contains:
30 g of *Cistus* decoction
0.9 g of NaCl
0.02 g of benzalkonium chloride
70 g of water Example 2

100 ml of nasal spray contains:
50 mg of *Cistus* extract 4:1
0.9 g of NaCl
0.02 g of benzalkonium chloride 100 g of water Example 3

100 ml of nasal spray contains:
200 mg of *Cistus* extract 4:1
0.9 g of NaCl
0.02 g of benzalkonium chloride
100 g of water Example 4

100 ml of nasal spray contains:
60 g of *Cistus* extract
0.9 g of NaCl
40 g of water
0.02 g of benzalkonium chloride Example 5

100 ml of nasal spray contains:
100 g of *Cistus* extract
0.9 g of NaCl
0.02 g of benzalkonium chloride Example 6

100 ml of nasal spray contains:
100 mg of *Cistus* extract 4:1
0.9 g of NaCl
100 g of water
0.02 g of benzalkonium chloride Example 7

100 ml of nasal spray contains:
30 g of *Cistus* extract
0.9 g of NaCl
70 g of water Example 8

100 ml of nasal spray contains:
50 mg of *Cistus* extract 4:1
0.9 g of NaCl
100 g of water Example 9

100 ml of nasal spray contains:
200 mg of *Cistus* extract 4:1

0.9 g of NaCl
100 g of water

Example 10

100 ml of nasal spray contains:
60 g of *Cistus* extract
0.9 g of NaCl
40 g of water

Example 11

100 ml of nasal spray contains:
100 g of *Cistus* extract
0.9 g of NaCl

Example 12

100 ml of nasal spray contains:
100 mg of *Cistus* extract 4:1
0.9 g of Nadi
100 g of water

Example 13

100 ml of nasal spray contains:
0.4 g of *Cistus* extract 4:1
0.9 g of NaCl
0.4 g of benzoic acid
0.123 g of NaOH

Example 14

100 ml of nasal spray contains
0.4 g of *Cistus* extract 4:1
0.9 g of NaCl
0.12 g of potassium sorbate

The invention claimed is:

1. A method for treating influenza in a human in need thereof comprising administering nasally to said human in need thereof therapeutically effective amounts of a nasal spray of *Cistus incanus* extract, wherein said spray has a particle size of at least 30 micrometer.

* * * * *